United States Patent [19]

Faryniarz et al.

[11] Patent Number: 5,840,280
[45] Date of Patent: Nov. 24, 1998

[54] SILICONE COPOLYOL FORMULATED HAIRSPRAY COMPOSITIONS

[75] Inventors: Joseph Raymond Faryniarz, Oxford, Conn.; Susan Kay Hentrich, Alton, Ill.

[73] Assignee: Chesebrough-Pond's USA Co., Division of Conopco, Inc., Greenwich, Conn.

[21] Appl. No.: 655,171

[22] Filed: May 30, 1996

[51] Int. Cl.$^6$ ...................................................... A61K 7/11
[52] U.S. Cl. ........................... 424/47; 424/45; 424/70.11; 424/70.12; 424/DIG. 1; 424/DIG. 2; 528/30; 514/957
[58] Field of Search ................................. 528/30; 424/45, 424/47, 70.11, DIG. 1, DIG. 2, 70.12; 514/957

[56] References Cited

U.S. PATENT DOCUMENTS

| | | | |
|---|---|---|---|
| 3,928,588 | 12/1975 | Robert | 424/234 |
| 4,423,041 | 12/1983 | Clum et al. | 424/184 |
| 4,871,529 | 10/1989 | Sramek | 424/47 |
| 5,115,049 | 5/1992 | Imperante et al. | 525/479 |
| 5,120,812 | 6/1992 | O'Lenick et al. | 528/28 |
| 5,294,437 | 3/1994 | Shah et al. | 424/70.11 |
| 5,620,684 | 4/1997 | Dupuis | 424/70.12 |
| 5,658,552 | 8/1997 | Bunning et al. | 424/45 |

FOREIGN PATENT DOCUMENTS

| | | |
|---|---|---|
| 669330 | 6/1991 | Australia . |
| 0 260 641 | 3/1988 | European Pat. Off. . |
| 0 635 258 | 1/1995 | European Pat. Off. . |
| 0 688 556 | 12/1995 | European Pat. Off. . |
| 920350603 | 12/1992 | Japan . |
| 5209147 | 8/1993 | Japan . |
| 92/21316 | 12/1992 | WIPO . |

*Primary Examiner*—Raj Bawa
*Attorney, Agent, or Firm*—Milton L. Honig

[57] ABSTRACT

A hairspray composition is provided with improved combability, spray efficiency and anti-foaming properties. The hairspray includes a film-forming resin, a carrier such as ethanol and a small level of a propoxylated non-ethoxylated silicone copolyol.

12 Claims, No Drawings

SILICONE COPOLYOL FORMULATED HAIRSPRAY COMPOSITIONS

BACKGROUND OF THE INVENTION

1. Field of the Invention

The invention concerns hairspray compositions formulated with certain silicone copolyols which improve hairstyling properties of the compositions.

2. The Related Art

Silicone copolyols also known in CTFA nomenclature as dimethicone copolyols have been reported in the literature and even commercially employed for hairsprays. Copolyols ease brushing, impart a soft feel, reduce stickiness of sprayed resin and impart luster to the hair. Among the commercial hairsprays containing dimethicone copolyol is Rave® Microspray introduced into the U.S. in 1995.

EP 0 116 207 (Elliott et al.) reports an aerosol hairspray formulation comprising a hair-holding resin dissolved in a solvent system such as ethanol and an aerosol propellant. Additionally present is from 0.5 to 10% by weight of at least one cyclic silicone such as dimethyl siloxane cyclic tetramer or dimethyl siloxane cyclic pentamer in addition to a dimethicone copolyol such as Dow Corning 193® surfactant.

The use of dimethicone copolyols in cosmetic and personal care formulations is discussed in a paper by F. C. Vick in Soap/Cosmetics/Chemical Specialties for May, 1984, Vol. 60 p. 36ff entitled "Structure/Property Relationships for Silicone Polyalkylenoxide Copolymer and Their Effects on Performance in cosmetics." The described copolymers discussed vary widely in molecular weight and content and type of alkylenoxy i.e. ethylenoxy or propylenoxy, units present.

U.S. Pat. No. 3,928,558 (Chessman et al.) teaches that certain polydimethylsiloxane-polyoxyalkylene block copolymers can be incorporated into hairspray compositions comprising a film forming resin in a cosmetic vehicle. These polymers have a silicon content of 15 to 25%, a molecular weight of from 1,200 to 5,000 and a viscosity at 25° C. of 3 to 10 poises. Their inclusion renders the resin easier to brush out from the hair. Cheeseman et al. teaches that all three variables are critical in obtaining effective block copolymers.

U.S. Pat. No. 4,423,041 (Clum et al.) teaches detackifying compositions for use in emulsion-type personal care compositions. They comprise a mixture of a silicone fluid which can be dimethylsiloxane cyclic tetramer or pentamer (CTFA name "Cyclomethicone") and a silicone wax in a ratio of from about 9:1 to 1:3. The silicone wax can be a dimethicone copolyol having a molecular weight of about 1,600 to about 2,000, but is required to be a solid or semi-solid at body temperature and must be insoluble in water and insoluble or only slightly soluble in cosmetic oils.

U.S. Pat. No. 4,871,529 (Sramek) reports that SILWET L-7602® surfactant—which contains a relatively high amount of hydrophobic dimethylsiloxane units relative to the siloxane units containing the hydrophilic polyethyleneoxide units—imparts autophobic properties to ethanolic solvent system hairspray compositions without the necessity for the use of large amounts of hydrophobic silicone compounds or polymers.

Although U.S. Pat. No. 4,871,529 finds significant benefits with certain silicone copolyols, these have been shown to be satisfactory only in systems with relatively low amounts of water. There has been a need to improve combability, spray efficiency and even anti-foaming properties in systems with relatively high water contents, for instance levels of water that exceed 10% by weight.

Accordingly, it is an object of the present invention to provide a hairspray composition with a silicone copolyol that improves combability and spray efficiency.

Another object of the present invention is to provide a hairspray composition with a silicone copolyol that avoids undesirable foaming in relatively high water content solvent systems.

These and other objects of the present invention will become more readily apparent through the following summary and detailed discussion.

SUMMARY OF THE INVENTION

A hairspray composition is provided including:
(i) from 0.5 to 10% by weight of a film-forming resin;
(ii) from 0.02 to 0.5% by weight of a propoxylated non-ethoxylated silicone copolyol; and
(iii) a cosmetically acceptable carrier present in an effective amount to deliver the resin and silicone copolyol onto the hair.

Hairspray compositions of the present invention can additionally include further amounts of a hydrophobic silicone compound or polymer. Illustrative are dimethylsiloxane cyclic pentamer, dimethylsiloxane cyclic tetramer or a low viscosity polydimethylsiloxane fluid of about 2.0, preferably no more than about 10 centistokes in viscosity at 25° C. and mixtures thereof. Amounts may range from 0.02% to 0.5% by weight of the total hairspray composition. More preferably, the ratio of the propoxylated silicone copolyol used herein and such hydrophobic silicone compound or polymer ranges from 3:1 to 1:3, preferably 2:1 to 1:2, optimally 1:1, with the total of both best ranging from 0.1% to 0.2% by weight of the hairspray composition.

DETAILED DESCRIPTION OF THE INVENTION

Now it has been discovered that propoxylated non-ethoxylated silicone copolyols can improve delivery of film-forming resins to hair. Compositions with these copolyols when sprayed onto the hair also enhance combability and minimize foaming.

A suitable propoxylated silicone copolyol for purposes of this invention can have the following structure:

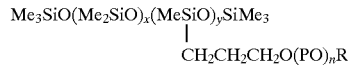

$$\text{Me}_3\text{SiO}(\text{Me}_2\text{SiO})_x(\text{MeSiO})_y\text{SiMe}_3$$
$$|$$
$$\text{CH}_2\text{CH}_2\text{CH}_2\text{O}(\text{PO})_n\text{R}$$

wherein
x has a value from 1 to 500;
y has a value from 1 to 500;
R is hydrogen or a $C_1$–$C_4$ alkyl;
n has a value from 1 to 400;
Me is methyl; and
PO is 1,2-propyleneoxy.

Preferably R will be an alkyl group, most especially a butyl group. Molecular weight of the copolyols may range from 500 to 30,000, preferably from 1,000 to 10,000, optimally from 2,000 to 5,000. Illustrative of the present invention is Silwet® L-7500 having a molecular weight of 3,000, with R being butyl.

Amounts of the propoxylated silicone copolyol may range from 0.02 to 0.5%, preferably from 0.05 to 0.3%, optimally from 0.075 to 0.3% by weight.

Propoxylated silicone copolyol of the present invention is effective at very low concentrations, as is evident from the recited concentration ranges. This has the advantage of minimizing cost while benefiting from combability, spray efficiency and even anti-foaming properties. Indeed, it is known that excess amounts of silicones can result in loss of "body", a term referring to the ability of hair to retain its styled appearance despite the effects of wind or head motion.

The hairspray resins employed in the compositions of the present invention should be capable of forming a film and holding the hair of the user in place after evaporation of solvent and other carrier volatile components. Hairspray resins are well known articles of commerce. They are typically resinous polymers which contain radicals rendering the polymers cationic, anionic, amphoteric or nonionic in nature. To provide optimum sprayability, the resins employed in hairspray compositions typically range in number average molecular weight of from 5,000 to 100,000, with 10,000 to 50,000 being more preferred. Resins of number average molecular weights in the range of 10,000 to 50,000 are typically employed with pump dispensers.

Amounts of the hairspray resin will range from 0.5 to 10%, preferably from 2 to 6% by weight.

Examples of anionic hairspray resins are copolymers of vinyl acetate and crotonic acid, terpolymers of vinyl acetate, crotonic acid and a vinyl ester of an alpha-branched saturated aliphatic monocarboxylic acid such as vinyl neodecanoate, and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as terpolymers of methacrylic acid, butylacrylate and ethyl methacrylate which is presently the preferred acrylic polymer. Another example of an acrylic polymer which can be employed in the compositions of the present invention is a polymer of tertiary-butyl acrylamide, acrylic acid and ethyl acrylate which is commercially sold by BASF Corp. under the name ULTRAHOLD 8 (CTFA—Cosmetic, Toiletry and Fragrance Association, designation: Acrylate/Acrylamide Copolymer).

Amphoteric polymers of the present invention can contain cationic radicals derived from monomers such as t-butyl aminoethyl methacrylate as well as carboxyl radicals derived from monomers such as acrylic acid or methacrylic acid. A suitable amphoteric polymer which can be used in the present invention is sold under the trademark AMPHOMER by National Starch and Chemical Corporation, identified by the CTFA name of Octylacrylamide/Acrylates/Butylaminoethyl Methacrylate Copolymer. Amphomer is described in U.S. Pat. No. 4,192,861 as being a polymer of N-tert-octyl acrylamide, methyl methacrylate, hydroxypropyl methacrylate, acrylic acid and t-butyl aminoethyl methacrylate.

Examples of nonionic hairspray resins are homopolymers of N-vinylpyrrolidone and copolymers of N-vinylpyrrolidone with compatible nonionic monomers such as vinylacetate and terpolymers of ethylacrylate, butylmethacrylate and methymethacrylate. Nonionic polymers based on N-vinylpyrrolidone are commercially available from the ISP Corporation. N-vinylpyrrolidone containing hairspray resins are taught in U.S. Pat. No. 3,914,403 to Valan.

Examples of cationic hairspray resins are copolymers of aminofunctional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylates and butyl acrylate. Cationic polymers containing N-vinylpyrrolidone are commercially available from ISP Corporation such as those sold under the trademark Copolymer 937.

As is known in the art, copolymers which contain carboxylic groups and are water insoluble are usually used in their neutralized water-soluble form. Suitable neutralizing agents which may be included in the hairspray compositions of the present invention are amines, especially amino alcohols, preferably 2-amino-2-methyl-1,3-propanediol and 2-amino-2-methyl-1-propanol (CTFA name is Aminomethyl propanol). Similarly, amine containing hair fixative polymers can be used in their acid salt form if it is desired to render them more water soluble.

Hairspray compositions of the present invention will also include a cosmetically acceptable liquid carrier for delivery of resin and silicone copolyol on to the hair. The carrier will include a solvent in which the resin is soluble. Ordinarily this will be a $C_1$–$C_4$ alkanol such as ethanol, isopropanol or tertiary-butanol, water and mixtures thereof. Most preferred is ethanol, especially mixtures of ethanol with water. Amounts of the carrier will range from 70 to 99%, preferably from 80 to 95% by weight. It is generally advisable to use the minimum amount of water; water tends to release the curls of the hair. For certain types of formulations, up to 30% of the solvent system may be water, preferably from 5 to 15% by weight.

Hairspray compositions of the present invention can be dispensed from containers which are propellant-charged aerosol containers or pump spray containers. These containers are well known to those skilled in the art. They are commercially available from various manufacturers such as American National Can Corp. and Continental Can Corp.

When the hairspray compositions are to be dispensed from pressurized aerosol containers, a propellant is necessary. The propellant may be mixed with the composition and can comprise from 10 to 80% by weight of the total hairspray composition. More preferably, between 20 and 50% of a volatile hydrocarbon propellant of the type commonly used in hairspray compositions is employed which can include liquified lower hydrocarbons of 3 to 4 carbon atoms such as propane, n-butane and isobutane. Examples of other propellants which can be employed are low boiling chlorofluorohydrocarbons such as trichlorofluoromethane, dichlorofluoromethane, and 1,2-dichloro-1,1,2,2-tetrafluoro ethane and mixtures thereof. Other examples of propellants are dimethylether, nitrogen and carbon dioxide. For ecological reasons, hydrocarbon propellants are generally preferred over chlorofluorohydrocarbons.

Alternatively, pressurized aerosol containers can be used where the propellant is separated from contact with the hairspray composition such as a two compartment can of the type sold under the trademark SEPRO from American National Can Corp.

The hairspray compositions are prepared in a conventional fashion. If a neutralizing agent is to be used, it is dissolved in the solvent and the resin is then added and mixed until a homogeneous solution is obtained. Alternatively, the resin can be dissolved in the solvent if it is sufficiently soluble to be dispersed without neutralization and then the neutralizing agents can be added. Otherwise, the resin is simply dissolved in the solvent and thereafter the silicone copolyol and any additional volatile silicone fluid can be added followed by any additional optional additives to modify the properties of the composition such as perfumes, plasticizers such glycols, phthalate esters and glycerine; emollients; lubricants and penetrants such as lanolin compounds; protein hydrolyzates and other protein derivatives; dyes, tints and other colorants; thickeners, anti-corrosion agents; panthenol, preservatives and the like. The order of addition of such optional ingredients is generally not critical.

Hairspray compositions of the present invention can also employ a $C_{12}$–$C_{30}$ long chain amine such as lauramidopropyl dimethylamine for neutralizing resins containing carboxyl groups. Preferably up to 40% of the carboxyl groups present in the resin are neutralized with the long chain amine and the remainder of the carboxyl groups are then neutralized with another water soluble amine such as aminomethyl propanol. Hairspray compositions possessing improved adhesion for the hair can be obtained through the use of such long chain amine neutralizing agents.

The following examples are provided to show various aspects of the present invention without departing from the scope and spirit of the invention. Unless otherwise indicated, all parts and percentages used in the Examples are by weight.

EXAMPLES 1–5

Compositions typical of the present invention are illustrated in the Table below.

| COMPONENT | EXAMPLE (WEIGHT %) | | | | |
|---|---|---|---|---|---|
| | 1 | 2 | 3 | 4 | 5 |
| Acrylates Copolymer | 7.5 | 5.5 | 6.0 | 4.0 | 5.0 |
| Lauramidopropyl Dimethylamine | 0.8 | 0.6 | 0.6 | 0.5 | 0.5 |
| Aminomethyl Propanol | 0.4 | 0.4 | 0.3 | 0.4 | 0.4 |
| Isodecyl Neopentanoate | 0.3 | 0.3 | 0.2 | 0.1 | 0.2 |
| Propoxylated Dimethicone Copolyol | 0.3 | 0.15 | 0.1 | 0.3 | 0.15 |
| Cyclomethicone | 0.15 | 0.15 | 0.2 | 0.2 | 0.15 |
| Ceteth-10 | 0.2 | 0.2 | 0.2 | 0.2 | 0.2 |
| Fragrance | 0.15 | 0.15 | 0.15 | 0.15 | 0.15 |
| Hair Keratin Amino Acids | 0.001 | 0.001 | 0.001 | 0.001 | 0.001 |
| Phytantriol | 0.01 | 0.01 | 0.01 | 0.01 | 0.01 |
| Benzophenone-4 | 0.01 | 0.01 | 0.01 | 0.01 | 0.01 |
| Sodium Chloride | 0.01 | 0.01 | 0.01 | 0.01 | 0.01 |
| Aloe Vera Gel | 0.002 | 0.002 | 0.002 | 0.002 | 0.002 |
| Vitamin E Acetate | 0.003 | 0.003 | 0.003 | 0.003 | 0.003 |
| Water | 11.5 | 13 | 15 | 10 | 9.5 |
| Ethanol | balance | balance | balance | balance | balance |

EXAMPLE 6

This Example evaluates the effect of different silicone copolyols on physical properties of the hairspray compositions. Dimethicone copolyols were incorporated into the following base formula.

| COMPONENT | WEIGHT % |
|---|---|
| Ethanol | 76.8 |
| Aminomethyl Propanol | 0.5 |
| Resyn ® 28-2930* | 4.5 |
| Deionized Water | 17.2 |

*Resyn ® 28-2930 is a carboxylated vinyl acetate terpolymer of vinyl acetate, crotonic acid and vinyl neodecanoate having 2% volatile content from National Starch and Chemical Corporation.

The following Silwet® dimethicone copolyols were incorporated into the above base formula each at levels of 0.075%, 0.15% and 0.3%: Silwet L-7500 (PO), Silwet L-7602 (EO) and Silwet L-7622 (EO). The resulting products were pressurized with 14% of A-75 propellant. Particle size analysis was performed on a Malvern Instrument, Mastersizer X. To understand the terminology, D(0,5), D(0, 1), and D(0,9) represent that 50%, 10% and 90% of the particle size are smaller than this value, respectively. D(4,3) represents the mean diameter derived from the volume distribution and D(3,2) or "sauter mean" represents the ratio of the total volume of the particles to the total surface area.

Spray foam characteristics were measured according to the Glass Slide Test. Product was sprayed 8 inches from a clean 1 inch by 3 inch glass microscope slide for two seconds. Compositions were then allowed to air dry and the appearance of the film upon drying was rated. The rating scale was as follows:

0=no foam
1=slightly foaming
2=somewhat foaming
3=more foaming

| Silicone Copolyols | d(0,5) | d(0,1) | d(0,9) | d(4,3) | d(3,2) | Foam Ratings |
|---|---|---|---|---|---|---|
| .075% Silwet L-7500 | 82.33 | 33.27 | 173.49 | 93.70 | 54.37 | 0 |
| .15% Silwet L-7500 | 81.27 | 32.29 | 176.24 | 93.57 | 53.37 | 0 |
| .30% Silwet L-7500 | 85.81 | 32.72 | 180.81 | 97.12 | 53.94 | 0 |
| .075% Silwet L-7602 | 90.29 | 34.86 | 184.81 | 100.76 | 56.37 | 2 |
| 0.15% Silwet L-7602 | 93.49 | 35.75 | 189.53 | 103.70 | 58.65 | 2 |
| .30% Silwet L-7602 | 100.27 | 38.13 | 204.52 | 111.16 | 64.31 | 2 |
| .075% Silwet L-7622 | 93.09 | 34.86 | 189.37 | 103.26 | 56.84 | 3 |
| .15% Silwet L-7622 | 101.68 | 36.58 | 204.97 | 111.63 | 60.87 | 3 |
| .30% Silwet L-7622 | 105.81 | 39.15 | 212.95 | 116.45 | 65.28 | 3 |

Foam rating values shown in the above table were excellent for Silwet L-7500, the fully propoxylated dimethicone copolyol. By contrast, formulations with Silwet L-7602 and L-7622 both being fully ethoxylated were found to have significant foaming problems. Silwet L-7500 was shown also to perform well in avoiding the negative attribute of increasing particle size.

What is claimed is:

1. A non-foaming hairspray composition comprising:
   (i) from 0.5 to 10% by weight of a film-forming resin having a number average molecular weight of from 5,000 to 100,000;
   (ii) from 0.02 to 0.5% by weight of a propoxylated non-ethoxylated silicone copolyol having molecular weight 500 to 30,000; and
   (iii) from 70 to 99% by weight of a cosmetically acceptable carrier selected from the group consisting of $C_1$–$C_4$ alkanol, water and mixtures thereof, the carrier being up to 30% water, to deliver the resin and silicone copolyol onto the hair.

2. The composition according to claim 1 wherein the silicone copolyol is present in an amount from 0.05 to 0.3% by weight.

3. The composition according to claim 1 wherein the resin is present in an amount from 2 to 6% by weight.

4. The composition according to claim 1 wherein the propoxylated non-ethoxylated silicone copolyol has the following structure:

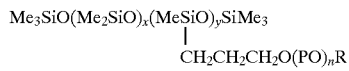
$$\begin{array}{c} Me_3SiO(Me_2SiO)_x(MeSiO)_ySiMe_3 \\ | \\ CH_2CH_2CH_2O(PO)_nR \end{array}$$

wherein
  x has a value from 1 to 500;
  y has a value from 1 to 500;
  R is hydrogen or a $C_1$–$C_4$ alkyl;
  n has a value from 1 to 400;
  Me is methyl; and
  PO is 1,2-propyleneoxy.

5. The composition according to claim 4 wherein R is butyl.

6. A hairspray composition comprising:
  (i) from 0.5 to 10% by weight of a film-forming resin selected from the group consisting of copolymers of vinyl acetate and crotonic acid; terpolymers of vinyl acetate, crotonic acid and a vinyl ester of an alpha-branched saturated aliphatic monocarboxylic acid; copolymers of methyl vinyl ether and maleic anhydride esterified with a saturated aliphatic alcohol containing from 1 to 4 carbon atoms; acrylic copolymers and terpolymers containing acrylic acid or methacrylic acid; Acrylate/Acrylamide Copolymer; Octylacrylamide/Acrylates/Butylaminoethyl Methacrylate Copolymer; homopolymers of N-vinylpyrrolidone; copolymers of N-vinylpyrrolidone with vinyl acetate; terpolymers of ethylacrylate, butylmethacrylate and methylmethacrylate; copolymers of dimethylaminoethylmethacrylate with N-vinyl pyrrolidone or alkyl methacrylates; and mixtures thereof;
  (ii) from 0.02 to 0.5% by weight of a propoxylated non-ethoxylated silicone copolyol; and
  (iii) from 70 to 99% by weight of a cosmetically acceptable carrier selected from the group consisting of $C_1$–$C_4$ alkanol, water and mixtures thereof to deliver the resin and silicone copolyol onto the hair.

7. The composition according to claim 6 wherein the film-forming resin is Octylacrylamide/Acrylates/Butylaminoethyl Methacrylate Copolymer.

8. The composition according to claim 1 wherein the alkanol is ethanol.

9. The composition according to claim 6 wherein the alkanol is ethanol.

10. The composition according to claim 1 which is dispensed from an aerosol or a pump spray container.

11. The composition according to claim 6 which is dispensed from an aerosol or a pump spray container.

12. The composition according to claim 1 wherein water is present from 5 to 15% by weight of the carrier.

* * * * *